(12) United States Patent
Calouche et al.

(10) Patent No.: US 12,214,190 B2
(45) Date of Patent: Feb. 4, 2025

(54) SYSTEM OF METHOD FOR TREATMENT OF HYPERHIDROSIS BY TAP-WATER IONTOPHORESIS AND ELECTROTHERAPY USING AN IMPROVED ELECTRODE

(71) Applicants: Maxime Calouche, Montreal (CA); Nicolas Jolicoeur, Montreal (CA)

(72) Inventors: Maxime Calouche, Montreal (CA); Nicolas Jolicoeur, Montreal (CA)

( * ) Notice: Subject to any disclaimer, the term of this patent is extended or adjusted under 35 U.S.C. 154(b) by 945 days.

(21) Appl. No.: 17/282,909

(22) PCT Filed: Oct. 7, 2019

(86) PCT No.: PCT/CA2019/000140
§ 371 (c)(1),
(2) Date: Apr. 5, 2021

(87) PCT Pub. No.: WO2020/069596
PCT Pub. Date: Apr. 9, 2020

(65) Prior Publication Data
US 2022/0008721 A1 Jan. 13, 2022

Related U.S. Application Data

(60) Provisional application No. 62/741,592, filed on Oct. 5, 2018, provisional application No. 62/741,608, filed
(Continued)

(51) Int. Cl.
*A61N 1/32* (2006.01)
*A61N 1/04* (2006.01)
(Continued)

(52) U.S. Cl.
CPC .......... *A61N 1/325* (2013.01); *A61N 1/0428* (2013.01); *A61N 1/08* (2013.01); *A61N 1/30* (2013.01); *A61N 1/044* (2013.01)

(58) Field of Classification Search
CPC ........ A61N 1/325; A61N 1/0428; A61N 1/08; A61N 1/30; A61N 1/044; A61N 1/048
See application file for complete search history.

(56) References Cited

U.S. PATENT DOCUMENTS 3,792,700 A * 2/1974 Sarnoff ................ A61B 5/0006
600/384
4,141,359 A * 2/1979 Jacobsen ................ A61N 1/325
604/20
(Continued)

*Primary Examiner* — Bradley J Osinski
(74) *Attorney, Agent, or Firm* — PRAXIS

(57) ABSTRACT

In one embodiment of the present invention, a method and system for the safe use of a tap-water iontophoresis machine is provided. The method is based on the specific treated zone by establishing several different treatment safety parameters according to which treated body zone is selected, such as the hands, feet, or armpits. The system includes a microcontroller, a voltage measuring module, current measuring module, polarity inversion module, and an optional resistance measuring module. The microcontroller adjusts the treatment based on the following: (a) the profile selected; (b) the values embedded in the microcontroller that is associated to the profile selected; and, (c) the values measured by the different modules and the time kept by the microcontroller. By simply choosing the treated zone, the device automatically adjusts these parameters to better reflect the specific particularities of that zone and establish often narrower ranges of values and increase safety and comfort for the patient.

19 Claims, 14 Drawing Sheets

Related U.S. Application Data on Oct. 5, 2018, provisional application No. 62/741,629, filed on Oct. 5, 2018.

(51) Int. Cl.
*A61N 1/08* (2006.01)
*A61N 1/30* (2006.01)

(56) References Cited

U.S. PATENT DOCUMENTS

| | | | |
|---|---|---|---|
| 6,597,947 B1 * | 7/2003 | Inoue | A61N 1/30 604/20 |
| 2010/0082088 A1 * | 4/2010 | Fassih | A61K 9/0014 607/149 |

* cited by examiner

Current Rise Slope

FIG. 16G FIG. 16H

SYSTEM OF METHOD FOR TREATMENT OF HYPERHIDROSIS BY TAP-WATER IONTOPHORESIS AND ELECTROTHERAPY USING AN IMPROVED ELECTRODE

CROSS-REFERENCE TO RELATED APPLICATIONS

The present application claims priority on U.S. Patent Application Ser. No. 62/741,592 filed on Oct. 5, 2018, on U.S. Patent Application Ser. No. 62/741,608 filed on Oct. 5, 2018, and U.S. Patent Application Ser. No. 62/741,629 filed on Oct. 5, 2018, all of which are incorporated herein by reference in their entirety.

BACKGROUND OF THE INVENTION

1. Field of the Invention

The present invention generally relates to the treatment of hyperhidrosis but more particularly to the treatment of hyperhidrosis by tap-water iontophoresis and electrotherapy using an improved electrode.

2. Description of Related Art

Hyperhidrosis is a condition defined by abnormal excessive sweating that is not necessarily related to heat or exercise. Those affected can sweat so much that it soaks through their clothes or sweat can drip off their hands. Besides disrupting normal daily activities, this type of heavy sweating can cause social anxiety and embarrassment. Fortunately, treatment is available by way of an iontophoresis machine. Such machines are generally comprised of a power source, a controller, at least two electrodes, a material to contain the tap-water, and occasionally cables to connect the components as described in U.S. Pat. No. 5,246,417. The treatment is delivered by putting two body parts in contact, generally but not limited to hands, feet or armpits, with the electrodes protected by a conductive liquid-filled buffer material, and by passing an electrical current through the body zones following certain parameters which are:

a) current ramp-up rate at the beginning of a treatment;
b) current ramp-up rate after an inversion of polarity;
c) the range of acceptable resistance of the body;
d) the polarity inversion parameters;
e) the duration of the treatment;
f) the maximum allowable current value; and
g) the maximum allowable tension value.

Former iontophoresis machines had the same slope of current ramp-up rate at the beginning of treatment and at polarity independently of the body part that was treated and the same maximal allowable tension value between (20V DC-120V DC), independently of the zone treated. The maximal allowable tension value is the tension value beyond which the user cannot increase tension.

In pre-existing iontophoresis machines, the devices either deliver the treatment regardless of the resistance between the electrodes or have a defined limit of resistance outside of which the treatment is not delivered or only partially delivered. The defined limits are the same for all treatment zones (same resistance limits for hands, feet, and armpits). The device only operates at full capability with resistance values between 500 ohms and 50,000 ohms. These values are monitored by the controller, which adjusts the device when operating outside of these values in order to activate a variety of safety parameters such as auto shut down, lower allowable tension, lower allowable current, and the activation of the visual indicator light.

Prior art of iontophoresis machines either have the same polarity alternation parameters available to the user independently of the treated zone (some machines do not even offer automatic polarity change), or the same polarity changes regardless of the treated zone. Alternatively, the user has options for changing polarities at will during treatment.

In one example, Lattin and Spevak disclose in U.S. Pat. No. 4,406,658A (Iontophoretic Device with Reversible Polarity—1983) a machine that automatically changes polarity and uses ramp-ups and ramp-downs to lower the pain of the user and deliver current equally across both polarities.

In another example, Jacobsen et at disclose in U.S. Pat. No. 4,141,359 (Epidermal Iontophoresis Device—1979) a comparator circuit that monitors current flow and voltage across the electrodes and automatically triggers an SCR shutdown circuit when impedance readings are outside predetermined limits to prevent excessive voltage buildup and the accompanying dangers of shock and burns.

In yet another example, Domb et al. disclose in Patent Application No. WO 2005084748 A1 (Safe Device for Iontophoretic Delivery of Drugs—2005), that some devices can monitor impedance and make an automatic shutdown of the device when the value is outside a safe range. In their case, they evaluated the acceptable range to be a function of the treated surface area, but not in a predetermined way.

In yet another example, Morriss et al. disclose in U.S. Pat. No. 8,192,420B2 (Iontophoresis Methods—2012), an iontophoresis machine where the slope of the ramp-up in current is about 0.2 milliampere per second ($mA \cdot s^{-1}$). This greatly increases the comfort of the treatment: "The ramp-up rate is about 0.2 milliampere per second ($mA \cdot s^{-1}$). The ramp-up rate may have a stepped and positive slope. The final value may be less than about 1.0 milliampere (mA). The period of time may be between about 30 and 240 seconds (s)."

When it comes to the electrodes, the prior art teaches electrodes requiring multiple manufacturing operations and/or materials to be able to fasten a connector to an electrode, either by soldering, riveting, bending, drilling, etc., or by assembling a rubber electrode to a wire. All these techniques require different parts and different materials.

In one example, Bachinski and al. disclose in Patent Application No. US 2013/0023816 A1 (Electrodes, Electrode Systems, and Methods of Manufacture—2013) an electrode made of multiple layers of material, such as a conductive layer, a gel layer and a nonconductive bottom layer. In another example of the same patent, Bachinski and al. disclose an electrode where a button must be attached to the electrodes.

In another example, Zenkich discloses in U.S. Pat. No. 3,750,094 (Electrical Connector—1973) an electrode that necessitates a complex housing made of multiple parts.

Prior art electrodes also do not have a symmetrical thickness, and are often only usable on one side, making it difficult for an individual to apply the same level of pressure on both surfaces of the electrode when inserted in the armpit cavity. There is still a need for symmetrical electrodes that may be used on both sides wherein no assembly is required.

There is still a need for a safe method to use an iontophoresis machine that can give specifically adapted safety parameters according to the zone to be treated, because variables of skin resistance (ohms), skin sensitivity, buffer material available, and treated area (cm²) are different from one treated zone to another, as well as from one user to another.

Another drawback of the prior art is that most iontophoresis machines are primarily tension controlled. This method is simple, but one cannot control the dosage delivered in mA for a treatment because it can have different resistance load, thus different current value (in mA).

Current Controlled

Current controlled iontophoresis machines use current control instead of tension control, by allowing the processing unit to adjust the tension quickly in order to balance the current at the desired strength. They are an improvement over the iontophoresis machines that were tension controlled because they make it easier to have an accurate treatment dosage between treatments and patients.

Pulsed Rate

Another innovation of the prior art is to offer pulsed current (1 kHz to 50 kHz) controlled iontophoresis machines. Pulsed current is a technology that has been shown to eliminate the pain and sensation without significantly affecting the efficiency of the treatment. The method to calculate the current in mA is to take the peak value of the DC pulsed current. The problem with this method is that it always relies on the peak current value. Thus, it cannot show an accurate value, and can be up to 50% inaccurate, which can mislead the operator into believing the current is up to 200% of the real value, because it does not take into account the period of the duty cycle where current is off or at a different value than peak value. This provides unreliable dosage values.

Current iontophoresis machines either do not show the accurate real-time current value when using pulsed current, or they always show a real-time current value but do not use pulsed current. This means that it is not possible for the patient to know the real dosage they are receiving when using the available pulsed current iontophoresis machine. Therefore, there is still a need for a method to control an iontophoresis machine that shows real-time current value when using pulsed current in order to obtain a more accurate value.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In one aspect of the invention, a method for treatment of hyperhidrosis by tap-water iontophoresis and electrotherapy using an improved electrode is provided, the method comprising steps: (a) providing a tap-water iontophoresis machine having a power supply, microcontroller, a voltage measuring module, a current measuring module, a polarity inversion module, an electrode for use with a body zone; (b) selecting a body zone of a user to be treated by the tap-water iontophoresis machine, wherein the body zone includes a possibly body zone selected from hands, feet, or armpits; (c) establishing a plurality of safety parameters specific to the selected body zone to be treated; and, (d) treating the selected body zone of the user via the electrode of the tap-water iontophoresis machine according to the plurality of safety parameters for a predetermined treatment duration.

In one embodiment, the plurality of safety parameters of step (c) includes: (i) a first different slope of a first current rise at a beginning period of the treatment for each of the possible body zones to be selected; (ii) a second different slope of a second current rise after an inversion of polarity for each of the possible body zones to be selected; (iii) a different range of acceptable resistance of the user for each of the possible body zones to be selected; (iv) a different polarity inversion parameter for each of the possible body zones to be selected; (v) determining the predetermined treatment duration for each of the possible body zones to be selected; (vi) predetermining a maximal treatment current adapted for each of the possible body zones to be selected; and, (vii) predetermining a maximal treatment tension adapted for each of the possible body zones to be selected.

In another aspect of the invention, a system for treatment of hyperhidrosis by tap-water iontophoresis and electrotherapy using an improved electrode is provided, the system comprising: a power source configured to be plugged into a power outlet; an electrode having a thickness, a length, and a width, the electrode configured for use with a body zone for treatment; a microcontroller; a connection having a diameter configured to connect the electrode to the microcontroller; a buffer material containing tap-water; a voltage measuring module; a current measuring module; and, a polarity inversion module.

In yet another aspect of the invention, a system for treatment of hyperhidrosis by tap-water iontophoresis and electrotherapy using an improved electrode is provided, the system comprising: a power supply; an electrode for use with a hand or foot; an underarm electrode; a case configured to retain the electrode; and, a towel configured to cover the electrode or the underarm electrode during use.

In yet another aspect of the invention, A system for treatment of hyperhidrosis by tap-water iontophoresis and electrotherapy using an improved electrode is provided, the system comprising: a display showing an RMS, real-time current measurement when using a pulsed current.

The foregoing has outlined rather broadly the more pertinent and important features of the present disclosure so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present disclosure. It should be realized by those skilled in the art that such equivalent structures do not depart from the spirit and scope of the invention as set forth in the appended claims.

BRIEF DESCRIPTION OF TIE SEVERAL VIEWS OF THE DRAWINGS

Other features and advantages of the present invention will become apparent when the following detailed description is read in conjunction with the accompanying drawings, in which.

FIGS. 3A-E are various graphics showing different polarity inversion parameters per treatment profile (body zone) and the available tap-water.

Figure 4:
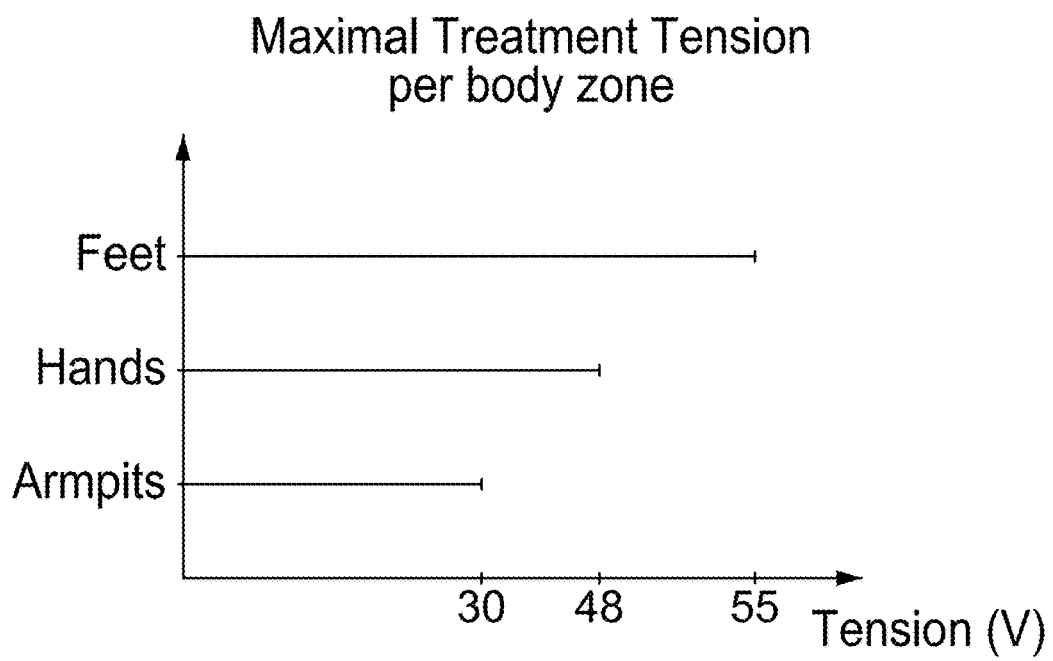

FIG. 4 is a graphic showing the predetermined maximum treatment tension allowed per body zone.

Figure 5:
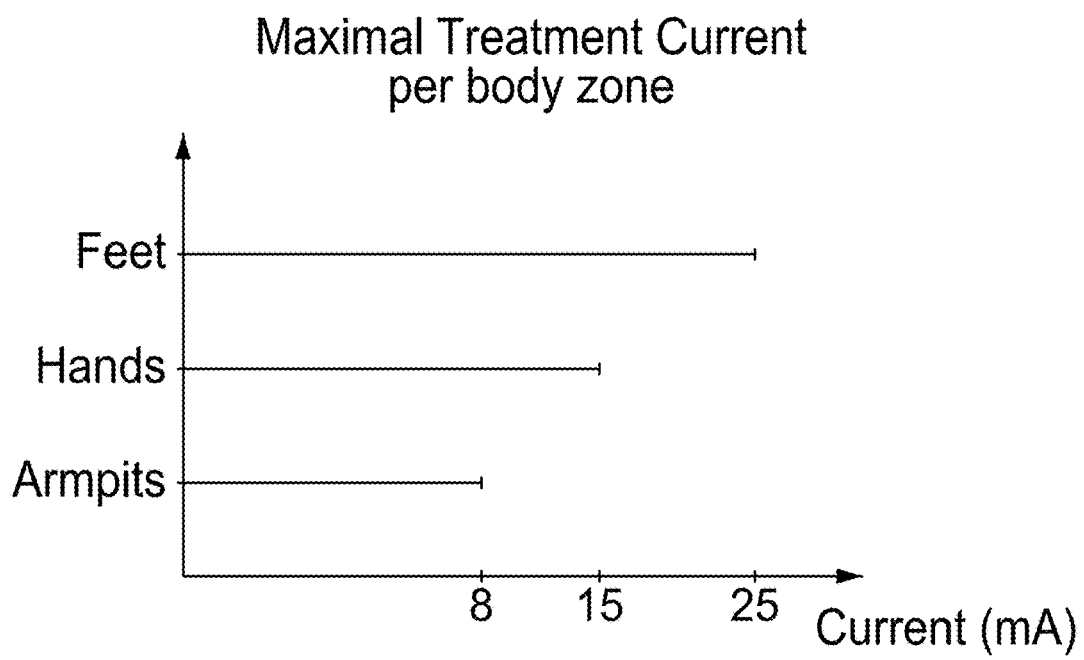

FIG. 5 is a graphic showing the predetermined maximum treatment current allowed per body zone.

Figure 6:
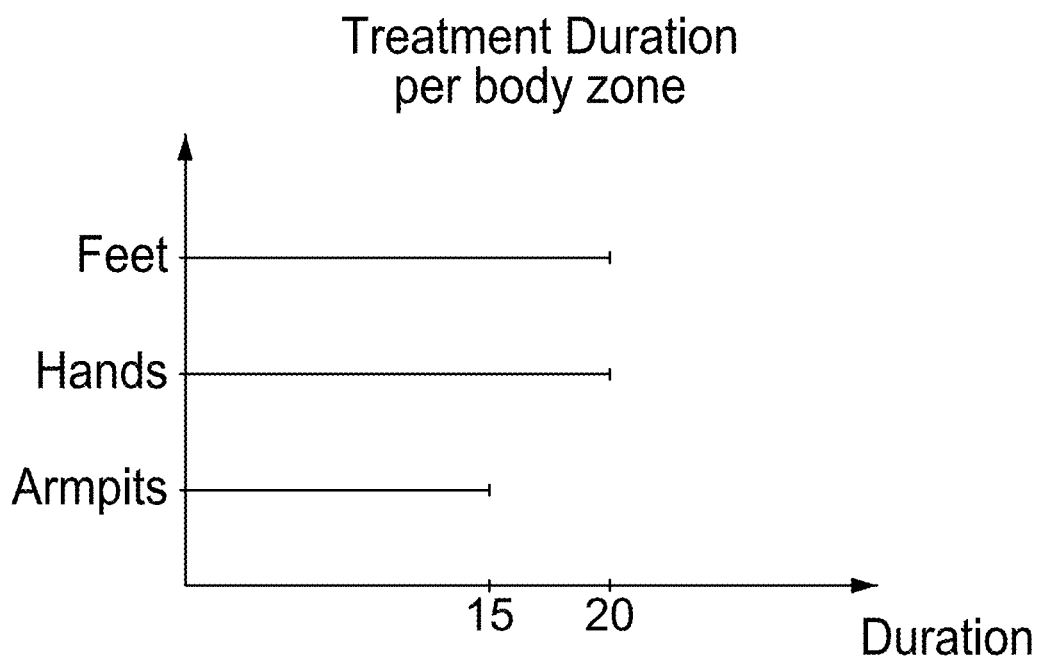

FIG. 6 is a graphic showing the predetermined duration of treatment duration per body zone.

Figure 7:
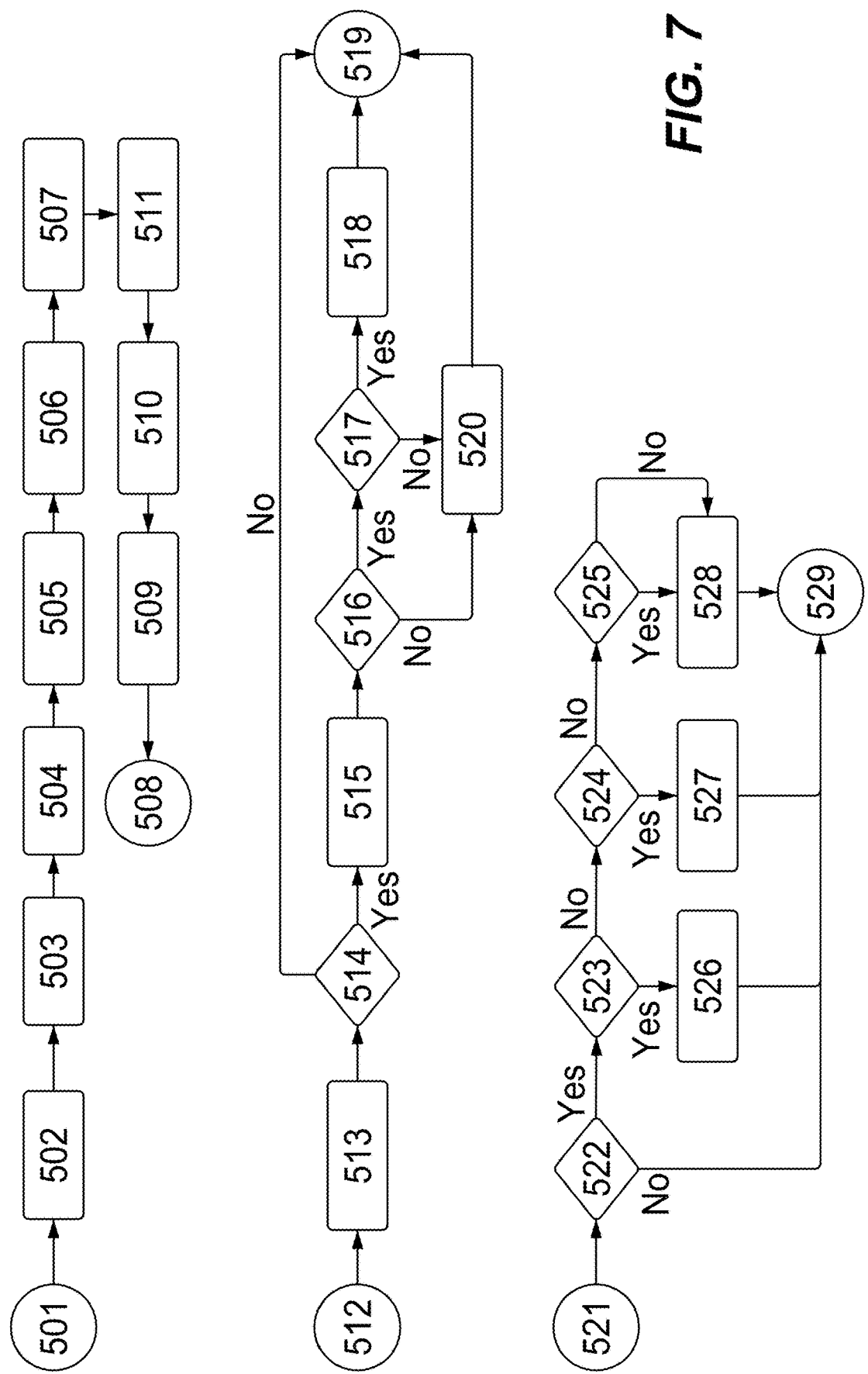

FIG. 7 is a flowchart of system firmware according to an embodiment of the present invention.

Figure 8:
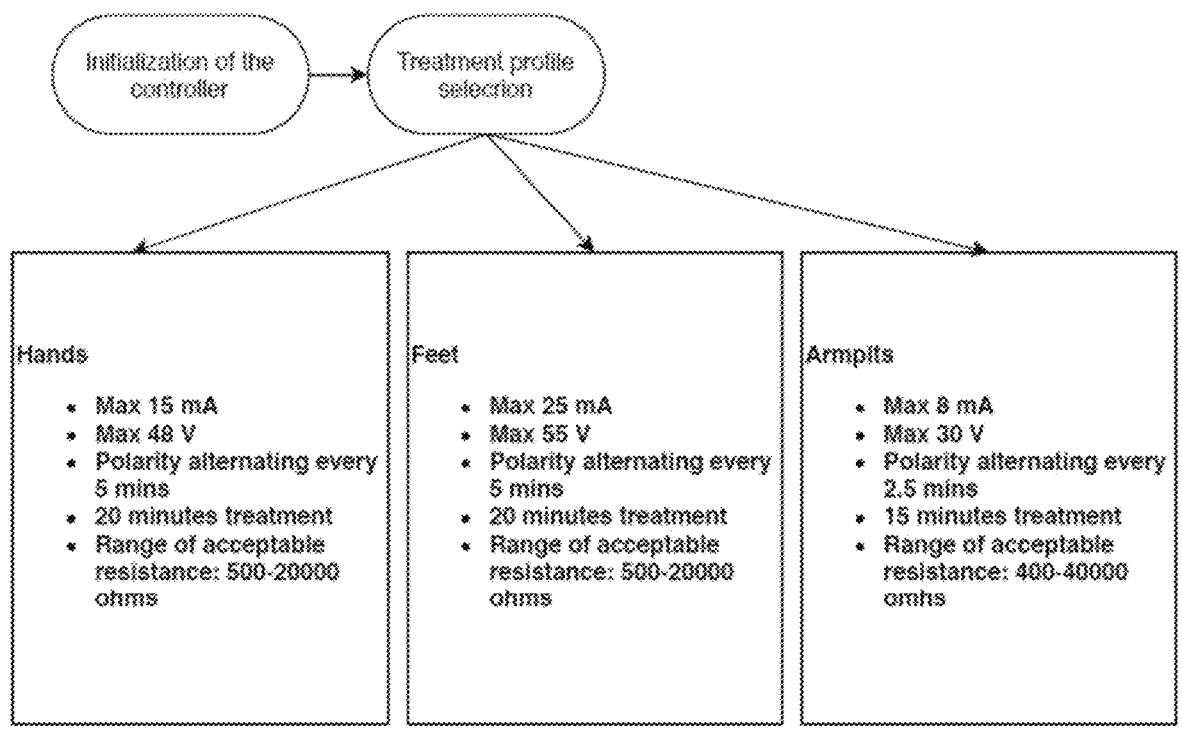

FIG. 8 is a schematic illustration of the recommended currents and voltages for various body zones according to an embodiment of the present invention.

Figure 9:
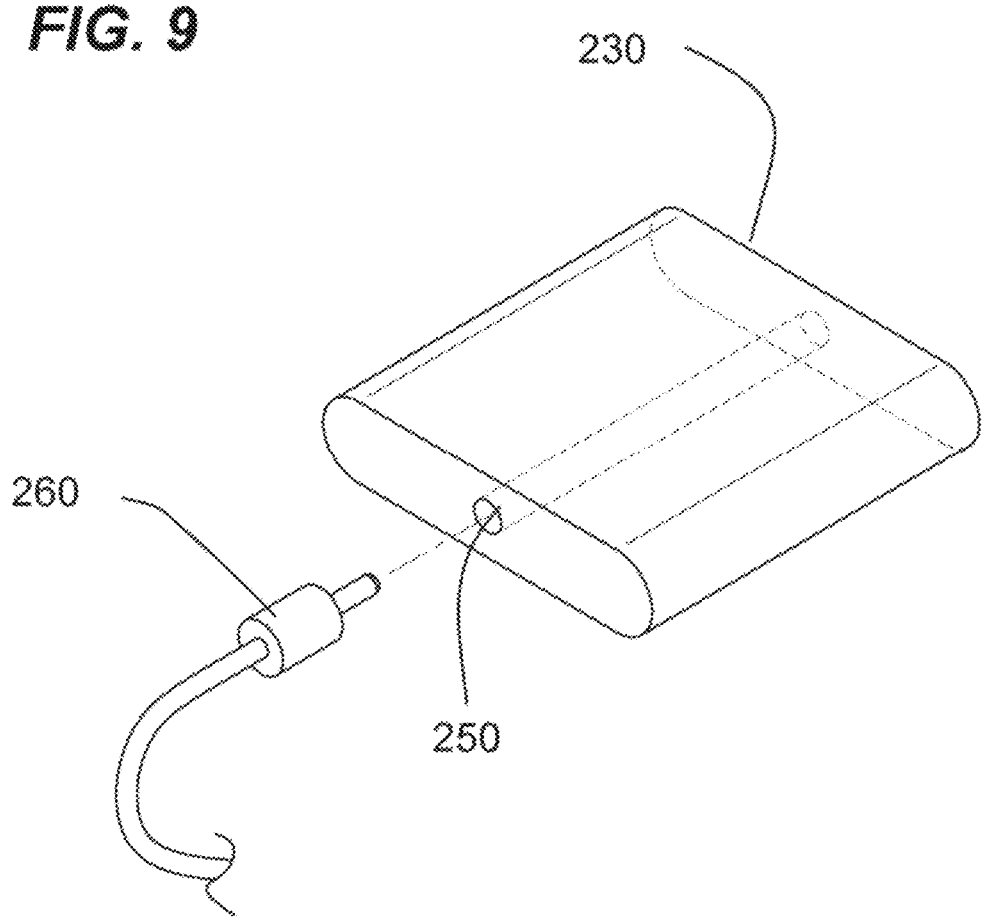

FIG. 9 is an isometric view of an electrode and an external male connector according to an embodiment of the present invention.

Figure 10:
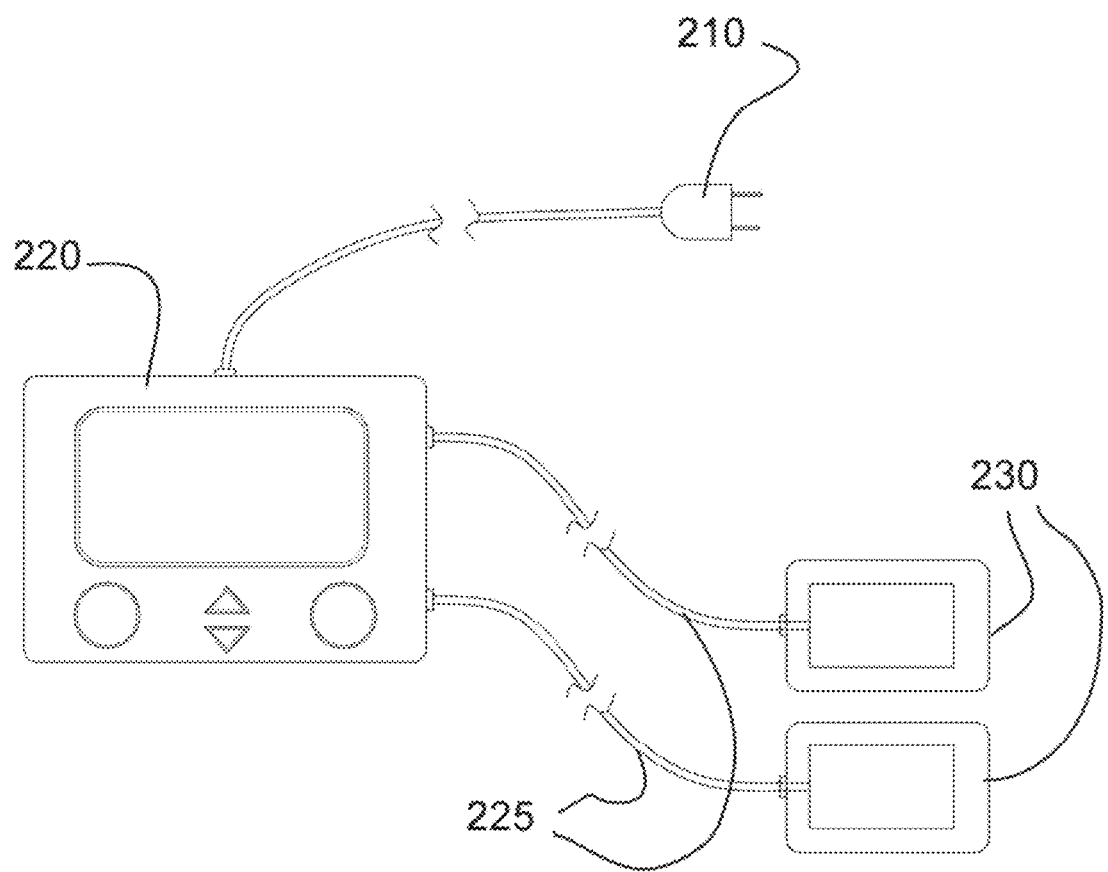

FIG. 10 is a plan view of a tap-water iontophoresis machine according to an embodiment of the present invention.

Figure 11:
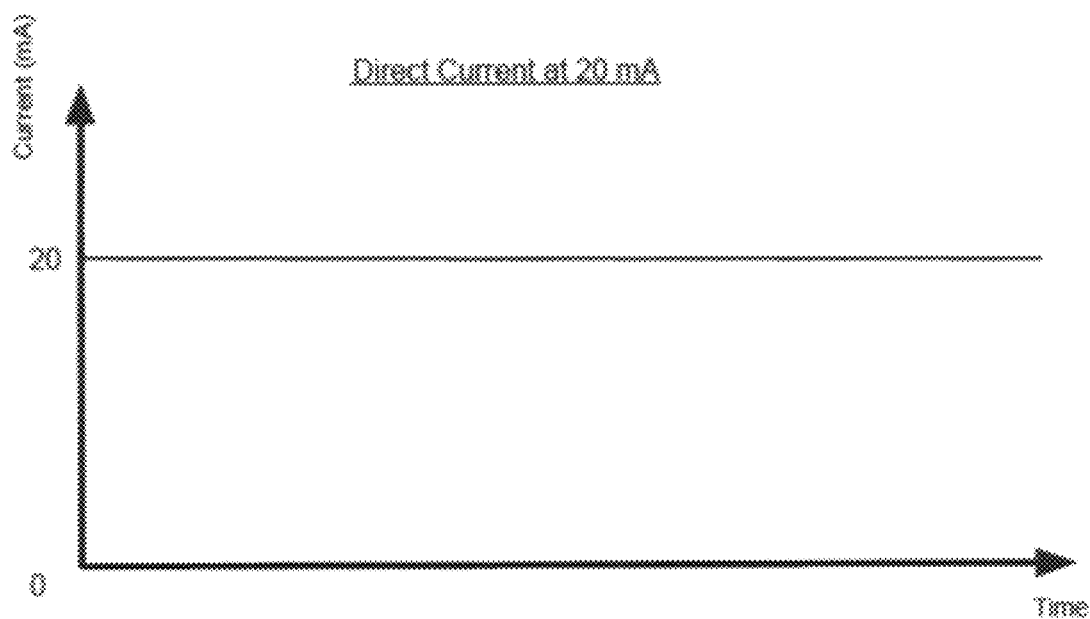

FIG. 11 is a graphic illustration of a Direct DC current over time according to an embodiment of the present invention.

Figure 12:
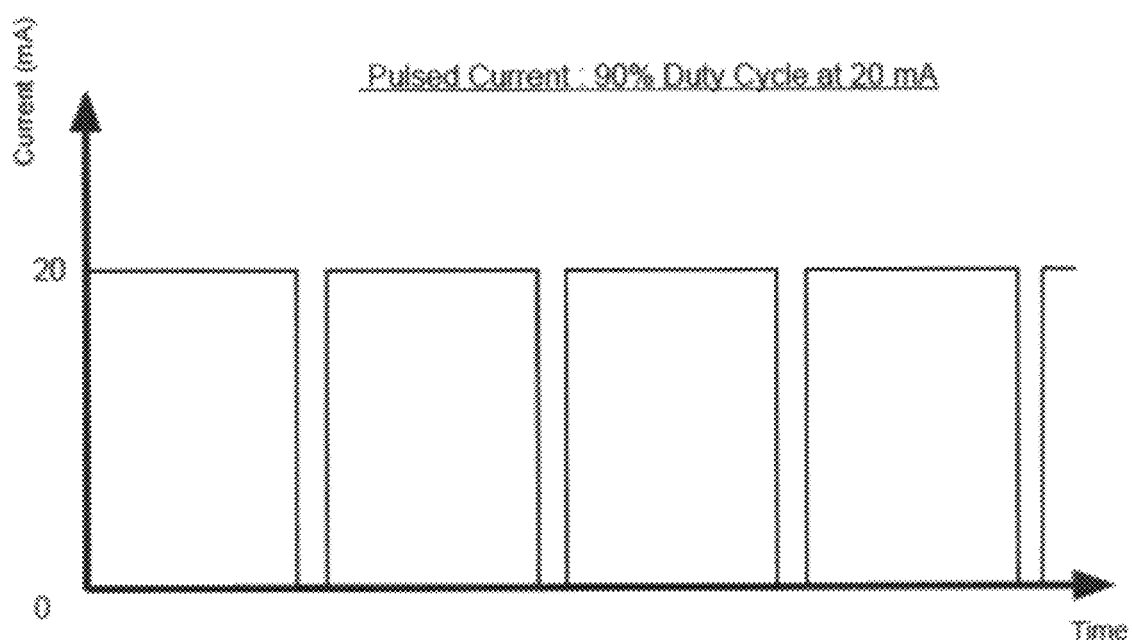

FIG. 12 is the graph of a pulsed current at a 90% duty cycle over time according to an embodiment of the present invention.

Figure 13:
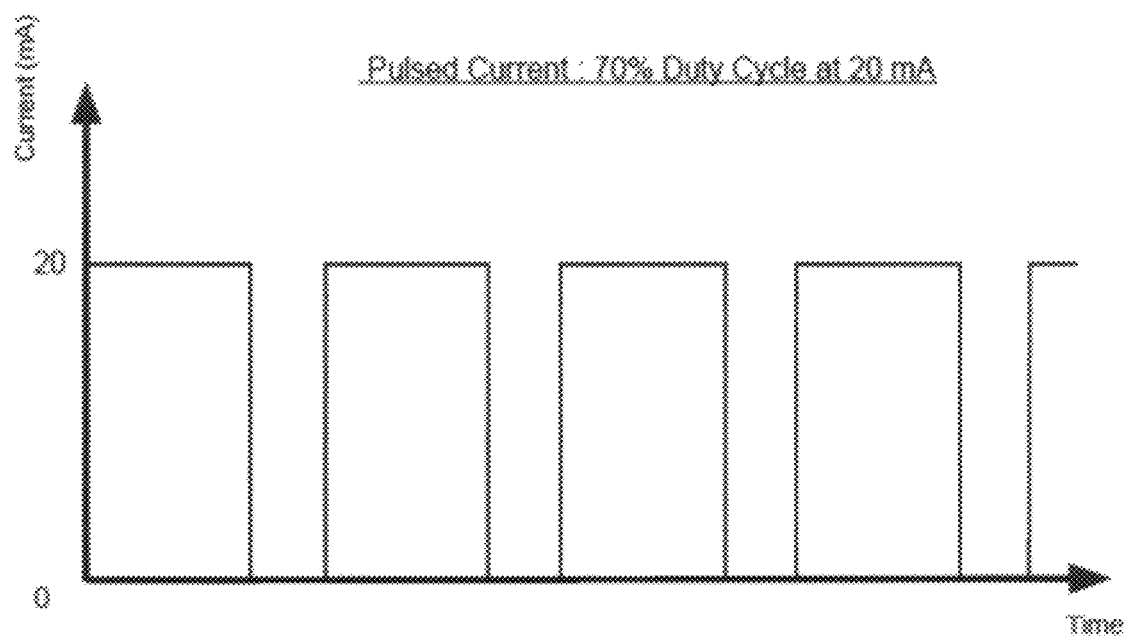

FIG. 13 is the graph of a pulsed current at a 70% duty cycle over time according to an embodiment of the present invention.

Figure 14:
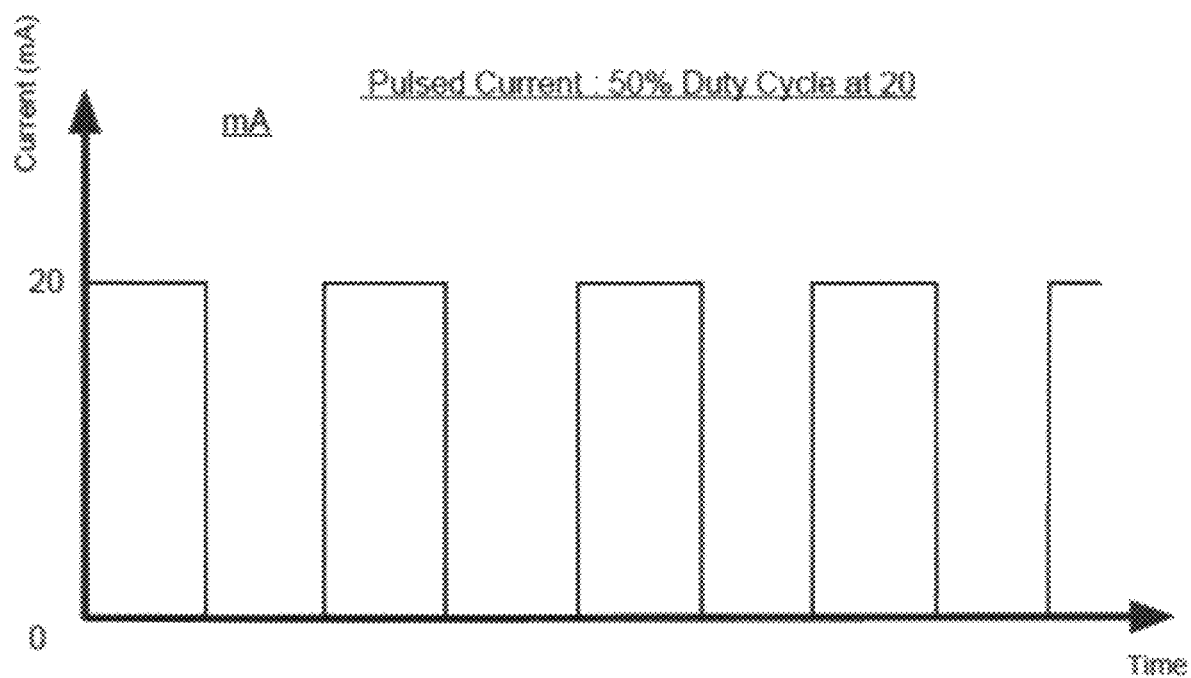

FIG. 14 is the graph of a pulsed current at a 50% duty cycle over time according to an embodiment of the present invention.

Figure 15:
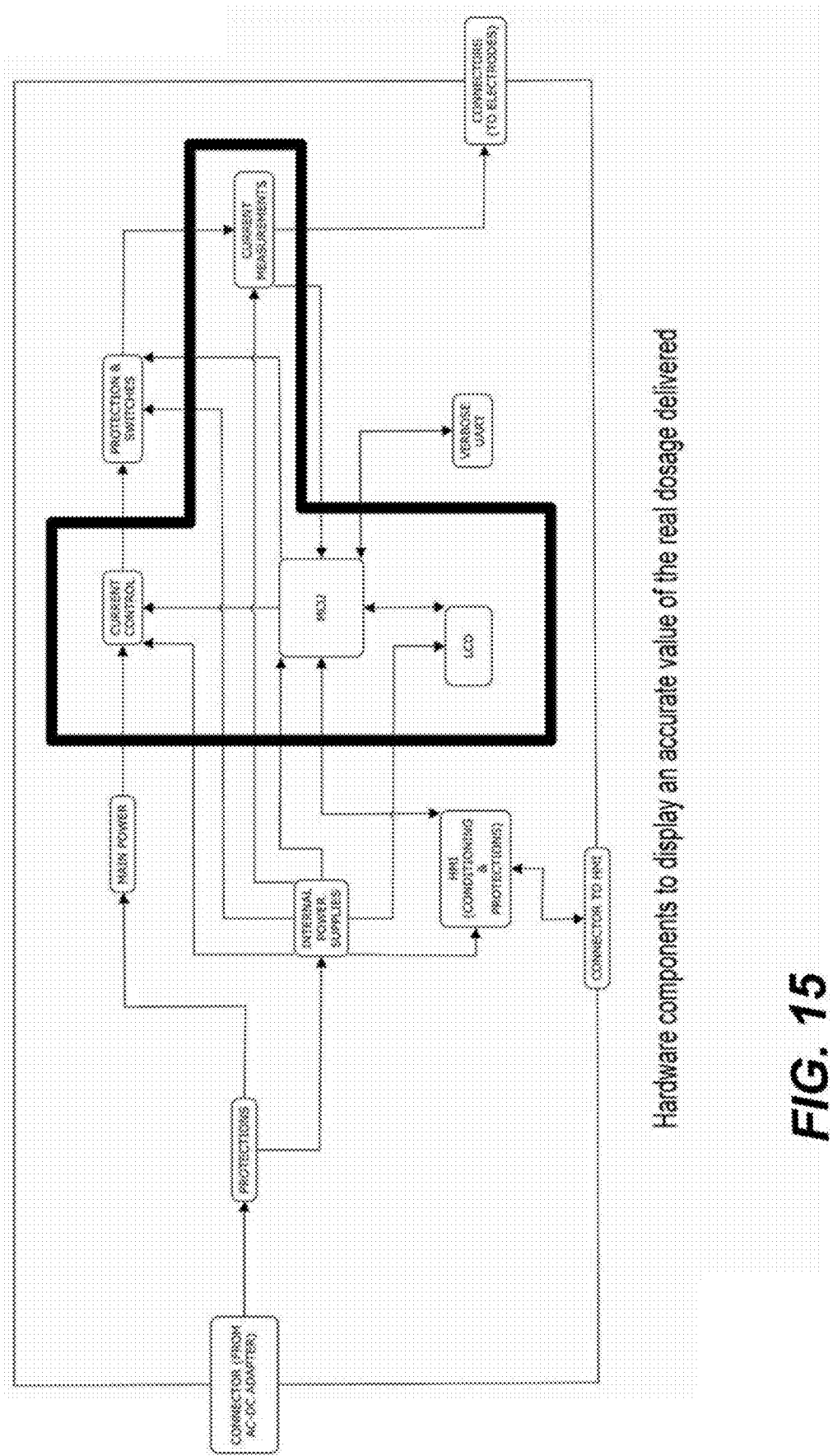
Figure 16A:
Figure 16B:
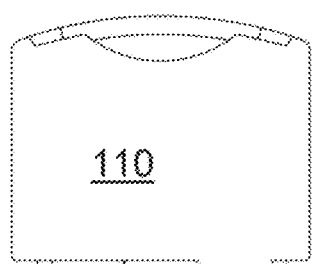
Figure 16C:
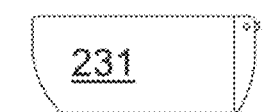
Figure 16D:
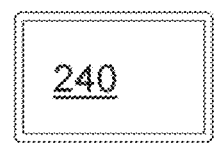
Figure 16E:
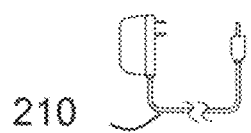
Figure 16F:
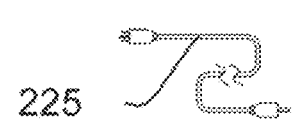
Figure 16F:
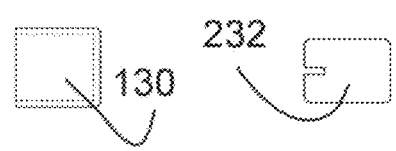
Figure 16I:
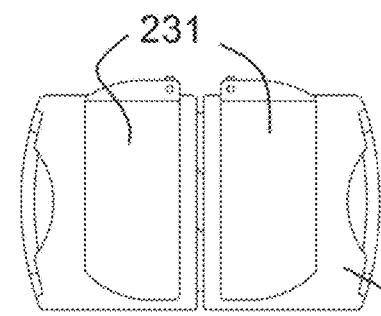
Figure 16K:
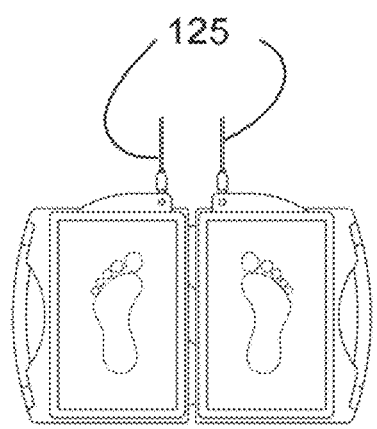
Figure 16J:
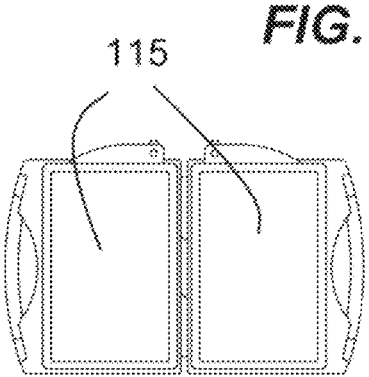

FIG. 15 is an architecture diagram of a hardware component of a modified iontophoresis machine according to an embodiment of the present invention.

FIGS. 16A-K are illustrative examples of all the components of the invention according to embodiments of the present invention.

Figure 17:
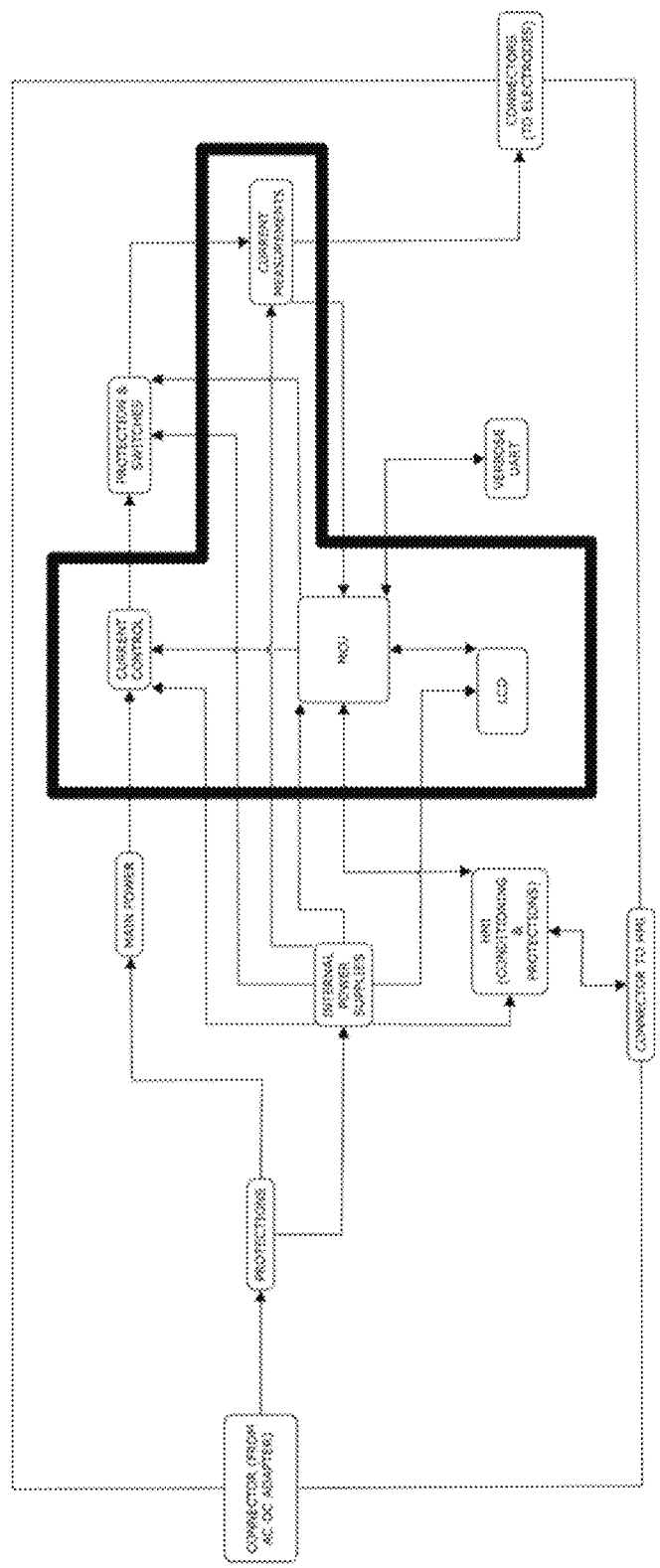

FIG. 17 is a schematic of the hardware components to display an accurate value of the real dosage delivered.

DETAILED DESCRIPTION OF THE PREFERRED EMBODIMENT

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein to specifically provide a system of method for treatment of hyperhidrosis by tap-water iontophoresis and electrotherapy using an improved electrode.

In one embodiment of the present invention, a method and system for the safe use of a tap-water iontophoresis machine according to the treated zone by establishing several different treatment safety parameters according to treated body zone independently from one treated zone to the other. The system comprises a microcontroller, a voltage measuring module, current measuring module, polarity inversion module, and an optional resistance measuring module.

The microcontroller adjusts the treatment based on the following: (a) the profile selected; (b) the values embedded in the microcontroller that is associated to the profile selected; and, (c) the values measured by the different modules and the time kept by the microcontroller. By simply choosing the treated zone, the device automatically adjusts these parameters to better reflect the specific particularities of that zone and establish often narrower ranges of values and increase safety and comfort for the patient.

In another aspect of the invention, anew method for the safe use of a tap-water iontophoresis machine according to the zone to be treated. The method comprising the following steps: (a) selecting the body zone to be treated such as hands, feet, or armpits, wherein the device automatically adjusts several predetermined parameters selected from the following: (b) current ramp-up at the beginning of treatment; (c) current ramp-up after an inversion of polarity; (d) the range of acceptable resistance of the body; (e) the polarity inversion parameters; (f) the treatment duration; (g) the maximal allowable current value; and (h) the maximal allowable tension value.

In one embodiment, the user starts treatment with the automatically adjusted values for safe tap-water iontophoresis use. In one embodiment of the present invention, the method further comprises establishing a plurality of safety parameters specific for each zone to be treated, the parameters being selected from the following: (a) different slope of the current rise at the beginning of treatment for each treatment profile (body zone), the slope further comprising 0.3 mA/s to 0.75 mA/s; (b) different slope of the current rise after the inversion of polarity for each treatment profile (body zone), the slope further comprising 0.2 mA/s to 0.425 mA/s; (c) different range of acceptable resistance of the body for each treatment profile (body zone), the range for acceptable resistance further comprising a minimum between 150-500 ohms and a maximum between 25,000-60,000 ohms for armpits, but preferably between 400-40000 ohms, and minimum between 300-750 ohms and a maximum between 15,000-25,000 ohms for hands and feet but preferably 500-20000 ohms for hands and feet;

(d) different polarity inversion parameters per treatment profile (body zone) and available tap-water, the polarity inversion further comprising polarity inversion set between 2 and 4 minutes, but preferably every 2.5 minutes for armpit, and between 4 and 10 minutes, but preferably every 5 minutes for hands and feet treatments; (e) predetermining the treatment duration adapted to the treatment profile (body zone), the treatment duration further comprising between 10 and 20 minutes for armpits, but preferably 15-minute and between 15 and 25 minutes for hands and feet, but preferably 20-minute; (f) predetermining the maximal treatment current adapted to the treatment profile (body zone), the current further comprising between 6 and 18 mA, but preferably 8 mA for armpits, and between between 12 and 20 mA, but preferably 15 mA for hands, and 25 mA for feet; and (g) predetermining the maximal treatment tension adapted to the treatment profile (body zone), the tension further comprising between 30 and 45 volts for armpits, but preferably 30 volts and between 45 and 55 volts, but preferably 48 volts for hands, and between 50 and 60 volts, but preferably 55 volts for feet.

In another embodiment of the present invention, the method further comprises different slopes of the current rise to the desired treatment current value at the beginning of treatment for each treatment profile (body zone) from 0.3 mA/s to 0.75 mA/s.

In another embodiment of the present invention, the method further comprises different slopes of the current rise to the desired treatment current value after an inversion of polarity for each treatment profile (body zone) from 0.2 mA/s to 0.45 mA/s. For example, the current rises faster when treating feet than when treating armpits, as the latter are more sensitive. The variation of the slope is an important factor that helps users reach a desired treatment current value with increased comfort, as well as the attenuation of the sensation of the polarity alternation.

In another embodiment of the present invention, the method further comprises different ranges of acceptable resistance of the body for each treatment profile (body zone). For example, the average resistance between armpits is not the same as the average resistance between hands. Thus, the potential resistance range should be adapted to the specific zone that is treated to ensure the user's safety. For example, it is common to see 30k ohms impedance in armpits, but it is not a normal value when treating hands or feet. Thus, the device may be made safer if we adapt the acceptable resistance range according to the treated zone.

In another embodiment of the present invention, the method further comprises different polarity inversion parameters per treatment profile (body zone) and the available tap-water. Since the quantity of tap-water used in the hands and feet treatments is not the same (acting as a buffer compared to the face or armpits), the frequency of polarity alternation must be changed to maintain a safe pH level in the water. Since pH changes faster during armpit treatment, the polarity also needs to be inverted faster to maintain the pH close to 7 in order to avoid chemical burns. For example, the polarity on hands and feet profiles may be changed every 5 minutes, but when treating armpits, the polarity may be changed every 2.5 minutes to avoid dangerous pH changes. The alternation of polarity is important and needs to be adapted to the specific sensitivity of the zone to be treated and to the amount of tap water available to mitigate the pH change. If the alteration of polarity is too frequent, the treatment becomes uncomfortable. If the alternation of polarity is not frequent enough, the tap water's pH can reach dangerous levels. Allowing users to choose the frequency of the polarity alternation by themselves may be subjective and thus not optimal for a uniform and safe treatment.

In another embodiment of the present invention, the method further comprises predetermining the treatment duration and offers automatic polarity alternation frequencies adapted to the treatment profile or body zone to be treated. The advantages of knowing the exact treatment duration and treated zone allows for the dosage received on each polarity to be balanced to give a more consistent result. This also keeps the pH level in a safe zone using the minimal amount of polarities alternations that cause user discomfort. When a user determines the duration of the treatment themselves, the risk is that the user can over-treat themselves and create erythema or skin irritation. Thus, having fixed duration times and adapted polarity alternation sessions by region is not only safer, but also provides a more uniform treatment because the current dosage is balanced across both polarities.

In another embodiment of the present invention, the method further comprises predetermining the treatment tension adapted to the treatment profile (body zone). In another embodiment of the present invention, the method further comprises predetermining the treatment current adapted to the treatment profile (body zone). In another embodiment of the present invention, the tap-water iontophoresis machine is further improved by the use of an electrode made out of a single piece of conductive material, that has an integrated female connector in the middle of a symmetric piece of conductive material that has a sufficient thickness so that it can house the female connector without affecting its structural integrity. It allows the two sides of the electrode to deliver current to the armpit. The female connector simply being a cylindrical hole in the piece of material, and the electrode being thick enough to fill the armpit cavity, wherein the electrode generally comprises the following: (a) a female connector made of a hole in the material; (b) better contact with skin as it fills the shape of the axillary cavity, and fewer problems with pressure points because of the symmetric shape of the electrode; (c) fewer parts and material used; (d) no assembly needed; and (e) fewer chances of breaking since it is made of only one piece of material.

In one embodiment of the present invention, the electrode is made of one single piece of conductive material. In another embodiment, the conductivity of the electrode material varies between 0.1 ohms and 50 ohms. In another embodiment of the present invention, the electrode further comprises a symmetric shape (in thickness) and a thickness sufficient enough to house a female connector. The electrode's symmetric shape and sufficient thickness further allow for a good fit in the axillary cavity, thus providing better skin contact and possibly preventing problems associated with pressure points or absence of contact. In another embodiment of the present invention, the new electrode further comprises a female connector made as a cavity in the material where a male connector may be fitted in. In another embodiment of the present invention, the electrode is made by extrusion of metal or another type of conductive material. In another embodiment, pulsed DC current (1 kHz to 50 kHz) or AC with DC-offset is used.

In another embodiment, the shortcomings of the prior art are generally mitigated by taking into account the mean value, the RMS or a combination of both the current when controlling and/or displaying the current. This enables the tap-water iontophoresis machine to display an accurate value of the real dosage delivered. It further allows for the calculation of the dosage in mA/minute and the calculation of the dosage in mA/minute/area.

Now the system and method of the present invention will be discussed in further details in Reference to the accompanying figures. Tap-water iontophoresis (TWI) machines of the prior art can be seen in FIG. 10, while FIGS. 16A-K shows components of the present invention. The prior art TWI machines and the present invention share some basic components including but not limited to power plug 210 configured to be plugged into a power outlet, a controller 220, cables 125/225 configured to connect the controller 220 to electrodes 230, and a buffer material 240, such as a foam, sponge, cotton, cloth or cellulose cable, containing a conductive liquid, in this case tap-water. Additional components include a carrier 110, a foot/foot electrode 115/231, and an armpit towel 130 for use with an armpit electrode 232.

As best seen in FIG. 9, an electrode 230 comprises a female connector 250 having a thickness to allow the female connector to be fitted therein. In one embodiment, the thickness of the electrode is between 3 mm and 30 mm, preferably 8 mm, and the female connector 250 includes a diameter between 1 mm and 10 mm, preferably 4 mm so that a standard 4 mm male jack can be fitted in. In one embodiment, the length of the electrode 230 is between 25 mm and 90 mm, preferably 45 mm and its width between 25 mm and 80 mm, preferably 40 mm in order to be conveniently used for hands and feet during treatment. In one embodiment, a male connector 260 is inserted into the female connector 250. It should be understood, that although a male jack connector is illustrated, other well-known types of connectors can be used without departing from the scope of the invention.

Hardware

In one embodiment, an output current monitor 270 is used for measuring the current as well as reading the voltage drop across a small value resistor (4.32 ohms), which acts as a current sensing resistor. This voltage is multiplied by a factor of 20 inside the current monitor so that the voltage at its output is a 20 V/V gain. This voltage is sent directly to a microcontroller 275 after being filtered by a low-pass filter. Additionally, the current monitor 270 can reject a PWM (Pulse-Width Modulation) signal, so that the voltage value is the RMS (Root Mean Square) value of the output signal. The rough hardware current calculation is as follows: output monitor voltage/(20*4.32).

Firmware

The firmware comprises a sampling frequency and strategy and the display of the current processing including a sampling frequency and strategy comprised of instant current, wherein an IRQ (Interrupt Request) is configured on ADC1 (Analog-to-Digital Converter) and the ISR (Interrupt Service Routine) is used to process the control loop. The number of samples within IRQ: 7 channels, 100 samples/channel. The clock frequency for ADC1: 12 Mhz and the IRQ frequency loop is defined as:

$$\frac{700}{12 \text{ Mhz}} * 20 = 1.16 \text{ ms} \quad (1)$$

In every 1.16 ms, the current is averaged (at this frequency, the current is considered has instant current), wherein the instant current equals equation (2) below (the value is stored in a 16 bit variable):

$$\frac{\sum_{0}^{99} ADC \text{ register } x}{100} \quad (2)$$

The instant current is converted current in mA, (milliamperes), wherein the converted current equals=(instant current*3.3 v/4095)/20*4.32. This value is stored in a float (32 bits) variable.

Displayed (on the display) current processing is processed as follows: (a) one sample every 10 ms (instant current rounded); and, (b) the average the last 50 samples.

Method of Use

An iontophoresis system using tap-water and method of use for treatment of a zone is comprised of the following steps: (a) selection of the zone to be treated; (b) automatic adjustment of the ramp-up of current at the beginning of treatment; (c) automatic adjustment of the ramp-up of current after an inversion of polarity; (d) automatic adjustment of allowable resistance range; (e) automatic adjustment of polarity inversion; (f) automatic adjustment of treatment duration; (g) automatic adjustment of the maximal current allowable; and (h) automatic adjustment of the maximal tension allowable.

In one embodiment, the zone to the treated in step (a) includes at least hands, feet, and armpits. In one embodiment, the ramp-up of current at the beginning of treatment in step (b) may be 0.5 mA/s. In one embodiment, the ramp-up of current after an inversion of polarity in step (c) may be 0.35 mA/s. In one embodiment, the allowable resistance in step (d) may range from 400 ohms to 40,000 ohms. In one embodiment, the treatment time during in step (f) may be 15 minutes for armpits and 20 minutes for hands and feet. In one embodiment, the maximum current in step (g) may be 8 mA. In one embodiment, the maximum tension in step (h) may be 30V.

Different slopes of the current rise to and from the desired treatment current value for each treatment profile (body zone): armpits current rise and hands current rise. The slope of the current rise of a treatment profile for armpits is slower than the slope for hands because of the sensitivity of the armpits. The slope of the current rise of a treatment profile for hands is faster than the slope for armpits. The current (in mA) rises faster than the slope of the treatment for armpits because the hands can tolerate a faster slope.

There is a different range of the body's acceptable resistance for each treatment profile or body zone: (a) the range of acceptable resistance for the treatment of feet; (b) the range of acceptable resistance for the treatment of hands; and (c) the range of acceptable resistance for the treatment of armpits.

Figure 1:
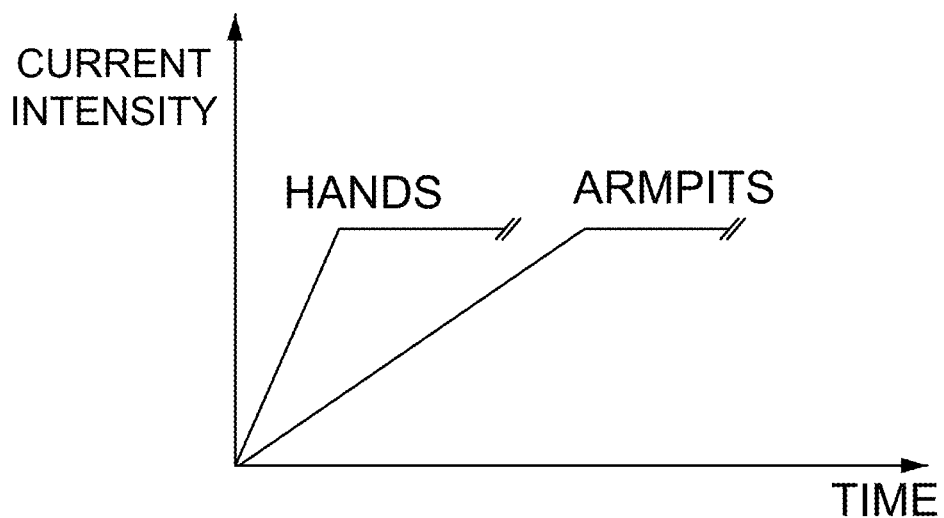
FIG. 1 is a graphic showing different slopes of the current rise for different body zones.
Figure 2:
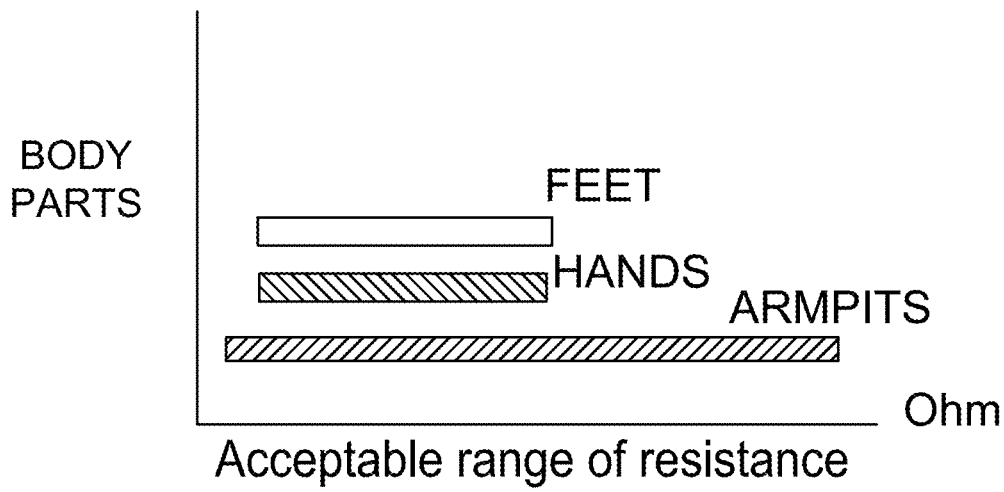
FIG. 2 is a graphic showing the different range of acceptable resistance of the body for each treatment profile (body zone).
Figure 3A:
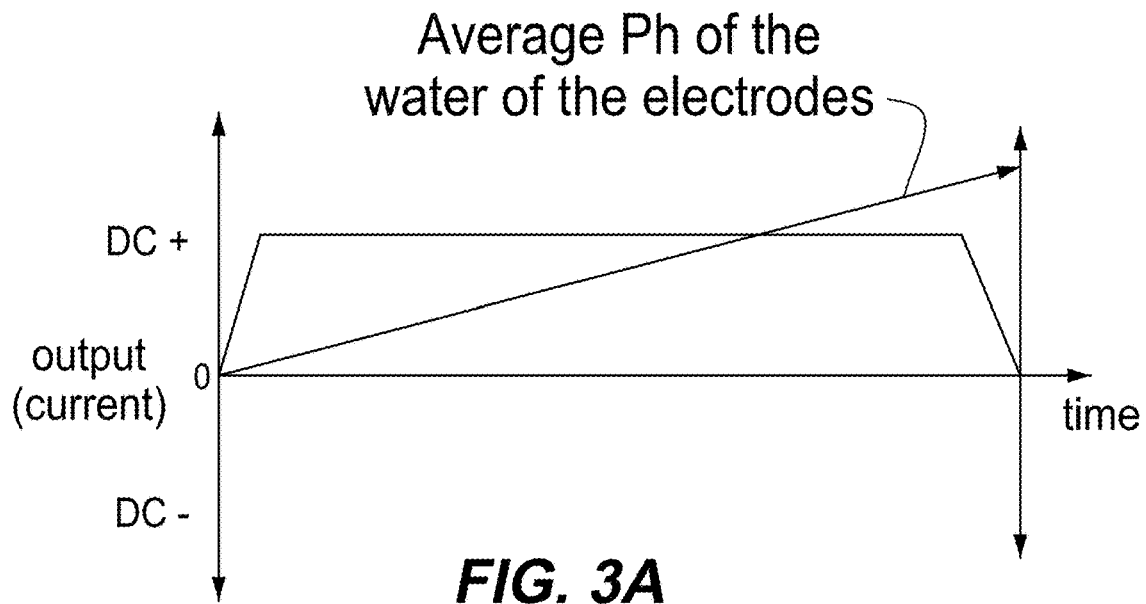
Figure 3B:
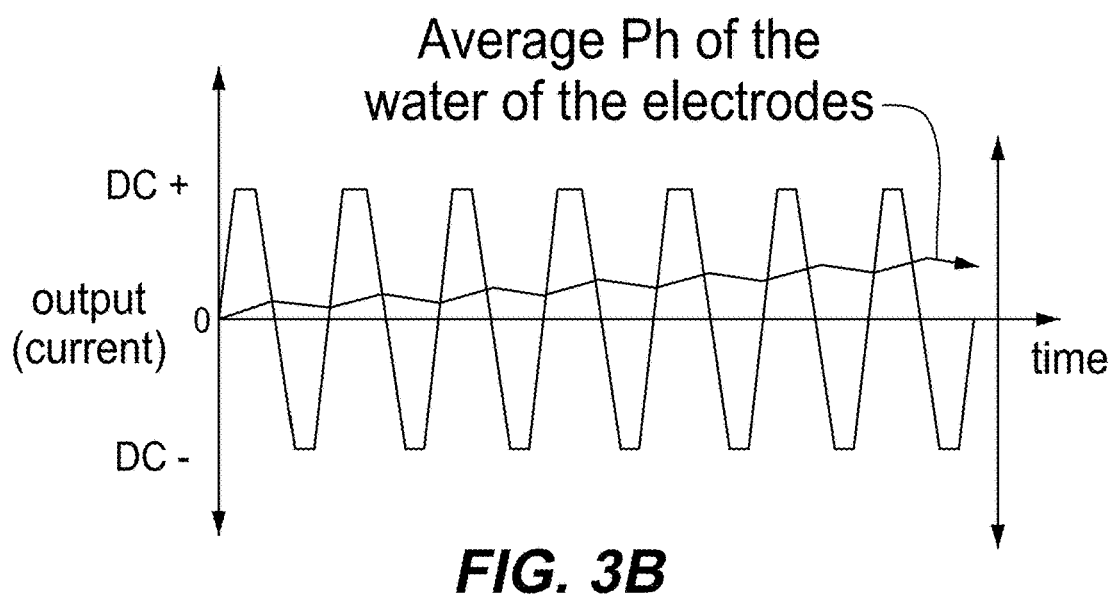
Figure 3C:
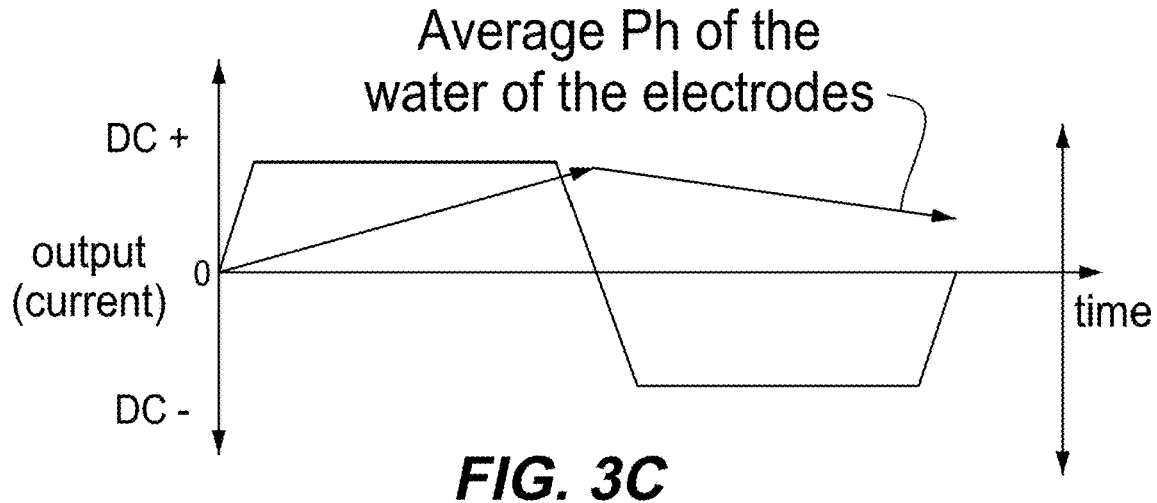
Figure 3D:
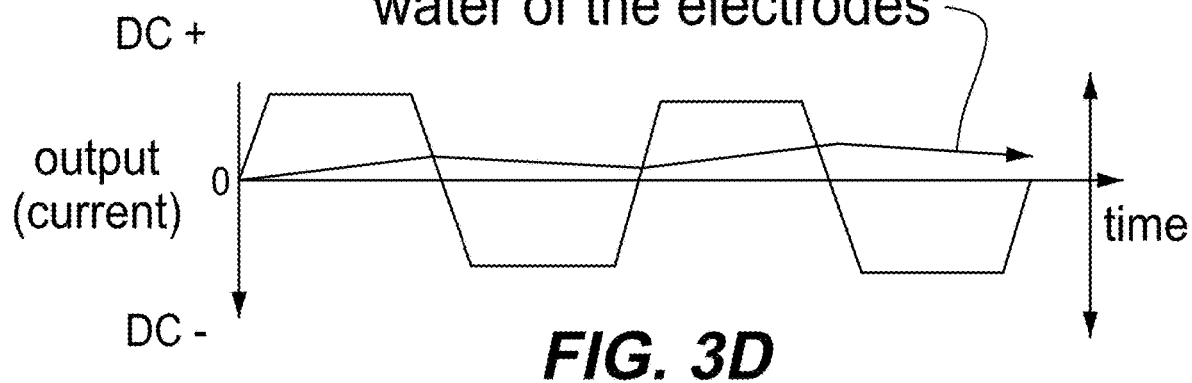
Figure 3E:
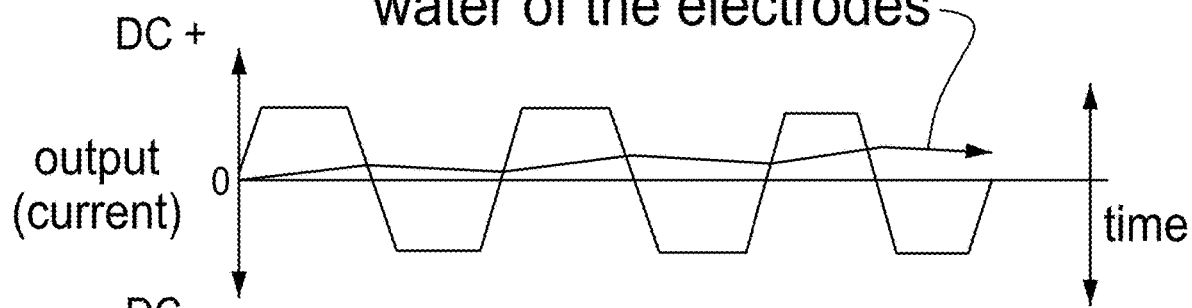

Referring now to FIGS. 3A-E, there is a different polarity alternation frequency adapted to the body zone and available tap-water to buffer the changes in pH. FIG. 3A shows the polarity (current output −/+) over time for an iontophoresis machine that never changes its polarity and shows the average pH in the water of both electrodes. These parameters may be used for any profile such as hands, feet, armpits, or any other profile. FIG. 3B shows the polarity (current output −/+) over time for an iontophoresis machine that changes its polarity very frequently and shows the average pH in the water of both electrodes. These parameters may be used for any profile such as bands, feet, armpits, or any other profile. FIG. 3C shows the polarity (current output −/+) over time for an iontophoresis machine that only changes the polarity once at the halfway point of the treatment and shows the average pH in the water of both electrodes. These parameters may be used for any profile such as hands, feet and armpits, or any other profile. FIG. 3D shows the polarity (current output −/+) over time for an iontophoresis machine with polarity alternation frequency adapted to hands and feet and shows the average pH in the water of both electrodes. FIG. 3E shows the polarity (current output −/+) over time for an iontophoresis machine with polarity alternation frequency adapted to armpits and the craniofacial region, and shows the average pH in the water of both electrodes.

FIG. 4 shows the predetermined maximal treatment tension allowed per body zone 400. The maximal tension for the treatment may be the following: (a) for the treatment of the feet, the maximum tension may be 55 volts; (b) for the treatment of the hands, the maximum tension may be 48 volts; and, (c) for the treatment of the armpits, the maximum tension may be 30 volts.

FIG. 5 shows the predetermined maximal treatment current allowed per body zone 500. The maximal current for the treatment may be the following: (a) for the treatment of the feet, the maximum current may be 25 mA; (b) for the treatment of the hands, the maximum current may be 15 mA; and, (c) for the treatment of the armpits, the maximum current may be 8 mA.

FIG. 6 shows the predetermined treatment duration per body zone. The treatment may be the following: (a) for the treatment of the feet, the treatment duration may be 20 minutes; (b) for the treatment of the hands, the treatment duration may be 20 minutes; and, (c) for the treatment of the armpits, the treatment duration may be 15 minutes.

FIG. 7 shows an example of system hardware architecture for programming the different safety parameters according to the body zone to be treated. These modifications may be used to adapt conventional iontophoresis machines to allow the implementation of the method described in the present invention for safe use of a tap-water iontophoresis machines according to the treated zone.

Best seen in FIG. 8, the present invention may further comprise different body zone treatment profiles according to selected body zone: hands, feet, or armpits.

In some embodiments, the system comprises a microcontroller, a voltage measuring module, a current measuring module, a polarity inversion module and optionally, a resistance measuring module. The microcontroller may further adjust the treatment based on the following: (a) the profile selected; (b) the values embedded in the microcontroller that is associated to the profile selected; and, (c) the values measured by the different modules, and the time kept by the microcontroller.

Referring now to FIGS. 11-14 various graphs are shown. FIG. 11 shows a graph illustrating the direct current (DC) over time, wherein the displayed current value is 20 mA. FIG. 12 shows a graph of a pulsed current at a 90% duty cycle over time, wherein the peak current value is 20 mA. FIG. 13 shows a graph of a pulsed current at a 70% duty cycle over time, wherein the peak current value is 20 mA. FIG. 14 shows a graph of a pulsed current at a 50% duty cycle over time, wherein the peak current value is 20 mA. The accurate value to display of the 90% duty cycle, the 70% duty cycle, and the 50% duty cycle is 18 mA, 14 mA, and 10 mA respectively, however other devices would display 20 mA based on the peak value of the pulsed current.

FIG. 15 is an architecture diagram of a hardware component of a modified iontophoresis machine according to an embodiment of the present invention, wherein the hardware component is configured to display an accurate value of the real dosage delivered during treatment.

Test work results using the iontophoresis machine of the present invention described herein are shown in the appendix to the specification.

FIG. 7 has the following sequence of operation:
Treatment manager 501
Configure profile max voltage 502
Configure loop detection protections (stage monitor) 503
Configure current and voltage protection 504
Activate proper polarity 505
Activate loop switch (stage monitor) 506
Take detection timestamp 507
Return 508
Enable the control in open loop 509
Activate PWM 510
Set the source voltage to <7V 511
Treatment manager (closed loop detection) 512
Retrieve current and voltage sensing info (stage monitor) 513
Current>0.1 mA 514
Calculate stage 2 impedance 515
Impedance>profile min. impedance 516
Impedance<Profile max. impedance 517
Close loop=TRUE 518
Return 519
Close loop=FALSE 520
Treatment Manager (profile cycling) 521
State=IDLE 522
Active Profile=Armpit 523
Active Profile=Hand 524
Active Profile=Feet 525
Active Profile=Armpit 526
Active Profile=Hand 527
Active Profile=Feet 528
Return 529

Although the invention has been described in considerable detail in language specific to structural features, it is to be understood that the invention defined in the appended claims is not necessarily limited to the specific features described. Rather, the specific features are disclosed as exemplary preferred forms of implementing the claimed invention. Stated otherwise, it is to be understood that the phraseology and terminology employed herein, as well as the abstract, are for the purpose of description and should not be regarded as limiting. Therefore, while exemplary illustrative embodiments of the invention have been described, numerous variations and alternative embodiments will occur to those skilled in the art. Such variations and alternate embodiments are contemplated, and can be made without departing from the spirit and scope of the invention.

In addition, reference to "first," "second," "third," and etc. members throughout the disclosure (and in particular, claims) are not used to show a serial or numerical limitation but instead are used to distinguish or identify the various members of the group.

What is claimed is:

1. A method for treatment of hyperhidrosis comprising:
   (a) selecting a body zone of a subject to be treated;
   (b) establishing a safety protocol specific to the selected body zone to be treated;
   (c) treating the selected body zone of the subject via electrical conduction according to the safety protocol, wherein the safety protocol comprises at least one parameter selected from the group of:
      (i) a first different slope of a first current rise at a beginning period of the treatment for each of the possible body zones to be selected;
      (ii) a second different slope of a second current rise after an inversion of polarity for each of the possible body zones to be selected;
      (iii) a different range of acceptable resistance of the subject for each of the possible body zones to be selected;
      (iv) a different polarity inversion parameter for each of the possible body zones to be selected;
      (v) determining a predetermined treatment duration for each of the possible body zones to be selected;
      (vi) predetermining a maximal treatment current adapted for each of the possible body zones to be selected;
      (vii) predetermining a maximal treatment tension adapted for each of the possible body zones to be selected; and
      any combination thereof
   (d) sampling in real time an electrical current dosage applied to the selected body zones in real time for a predetermined time interval thereby determining an instant current frequency thereof;
   (e) continuously and sequentially repeating the sampling of step (d) in real time to provide a contiguous series of a predetermined number of instant current frequencies;
   (f) averaging the predetermined number of instant current frequencies in of step (e) to determine an average current frequency; and
   (g) repeating steps (d) to (f).

2. The method of claim 1, wherein the body zone is selected from the group consisting of hands, feet, arm pits and combinations thereof.

3. The method of claim 2, wherein in (iii), the different range for acceptable resistance is a minimum between 150 and 500 ohms and a maximum between 25,000 and 60,000 ohms for armpits and minimum between 300 and 750 ohms and a maximum between 15,000 and 25,000 ohms for hands and feet.

4. The method of claim 2, wherein in (iv), the polarity inversion further comprising a polarity inversion set between 2 and 4 minutes for armpit treatments and between 4 and 10 minutes for hands and feet treatments.

5. The method of claim 2, wherein in (v), the predetermined treatment duration is between 10 and 20 minutes for armpits and between 1 and 25 minutes for hands and feet.

6. The method of claim 2, wherein in (vi) the maximal treatment current is between 6 and 18 mA for armpits, between 12 and 20 A for hands, and 25 mA for feet.

7. The method of claim 2, wherein in (vii), the maximal treatment tension is between 30 and 45 volts for armpits, and between 45 and 55 volts for hands and for feet.

8. The method of claim 1, wherein in (i), the first current rise is between 0.3 mA/s to 0.75 mA/s.

9. The method of claim 1, wherein in (ii), the second current rise is between about 0.2 mA/s to about 0.425 mA/s.

10. A system for hyperhidrosis treatment comprising:
an electrical power module for providing an electrical current;
an electrode in electrical communication with the electrical power module for being applied to selected body zones of a subject for electrical treatment thereof;
a controller comprising a processing unit with an associated memory of processor executable code and being in operative communication with the electrical power module and
a user interface in communication with the controller, wherein execution of the processor executable code provides for the processing unit to execute the computer implementable steps of:
(a) controlling the electrical power module during treatment of the selected body zones according to a safety protocol stored within the memory, wherein the safety protocol comprises at least one parameter selected from the group of:
(i) a first different slope of a first current rise at a beginning period of the treatment for each of the selected body zones;
(ii) a second different slope of a second current rise after an inversion of polarity for each of the selected body zones;
(iii) a different range of acceptable resistance of the subject for each of the selected body zones;
(iv) a different polarity inversion parameter for each of the selected body zones;
(v) determining a predetermined treatment duration for each of the selected body zones;
(vi) predetermining a maximal treatment current adapted for each of the selected body zones;
(vii) predetermining a maximal treatment tension adapted for each of the selected body zones; and any combination thereof;
b) sampling in real time an electrical current dosage applied to the selected body zones in real time for a predetermined time interval thereby determining an instant current frequency thereof;
c) continuously and sequentially repeating the sampling of step b) in real time to provide a contiguous series of a predetermined number of instant current frequencies;
d) averaging the predetermined number of instant current frequencies in of step c) to determine an average current frequency;
e) indicating in real time the average current frequency of step d) via the user interface; and
f) repeating steps b) to e).

11. A system according to claim 10, wherein the electrical power module provides for electrical current modulation.

12. A system according to claim 10, further comprising a voltage measuring module in operative communication with the electrical power module and the controller.

13. A system according to claim 10, further comprising a current measuring module in operative communication with the electrical power module and the controller.

14. A system according to claim 10, further comprising a resistance measuring module in operative in communication with the electrical power module and the controller.

15. A system according to claim 10, further comprising a polarity inversion module in operative communication with the electrical power module and the controller.

16. A system according to claim 10, wherein the electrical power module is in electrical communication with an electrical power supply.

17. A system for hyperhidrosis treatment comprising:
an electrical power module for providing an electrical current;
an electrode in electrical communication with the electrical power module for being applied to selected body zones of a subject for electrical treatment thereof;
a controller comprising a processing unit with an associated memory of processor executable code and being in operative communication with the electrical power module,
wherein execution of the processor executable code provides for the processing unit to execute the computer implementable step of:
controlling the electrical power module during treatment of the selected body zones according to a safety protocol stored within the memory, wherein the safety protocol comprises at least one parameter selected from the group of:
(i) a first different slope of a first current rise at a beginning period of the treatment for each of the selected body zones;
(ii) a second different slope of a second current rise after an inversion of polarity for each of the selected body zones;
(iii) a different range of acceptable resistance of the subject for each of the selected body zones;
(iv) a different polarity inversion parameter for each of the selected body zones;
(v) determining a predetermined treatment duration for each of the selected body zones;
(vi) predetermining a maximal treatment current adapted for each of the selected body zones;
(vii) predetermining a maximal treatment tension adapted for each of the selected body zones; and any combination thereof,
wherein the electrical power module comprises a male connector for being connected to the electrode, wherein the electrode comprises:
a single monolithic piece defining opposite body zone engaging faces and a peripheral surface interposed therebetween, the opposite body zone engaging faces providing for being applied to the selected body zones;

a female connector defining an opening in the peripheral surface leading to a channel within the single monolithic piece, wherein the female connector provides for receiving the male connector therein providing for the electrical power module to provide the electrical current to the opposite body zone engaging faces.

18. A system for hyperhidrosis treatment comprising:

an electrical power module for providing an electrical current;

an electrode in electrical communication with the electrical power module for being applied to selected body zones of a subject for electrical treatment thereof;

a user interface for indicating an electrical current dosage applied to the selected body zones during electrical treatment;

a controller comprising a processing unit with an associated memory of processor executable code and being in operative communication with the electrical power module and the user interface;

wherein during the electrical treatment, execution of the processor executable code provides for the processing unit to execute computer implementable steps of:

a) sampling in real time an electrical current dosage applied to the selected body zones in real time for a predetermined time interval thereby determining an instant current frequency thereof;

b) continuously and sequentially repeating the sampling of step a) in real time to provide a contiguous series of a predetermined number of instant current frequencies;

c) averaging the predetermined number of instant current frequencies in of step b) to determine an average current frequency;

d) indicating in real time the average current frequency of step c) via the user interface; and e) repeating steps a) to d).

19. An electrode for a hyperhidrosis treatment system comprising an electrical power module for providing an electrical current and comprising a male connector, the electrode providing for being in electrical communication with the electrical power module and for being applied to selected body zones of a subject for electrical treatment thereof, the electrode comprising:

a single monolithic piece defining opposite body zone engaging faces and a peripheral surface interposed therebetween, the opposite body zone engaging faces providing for being applied to the selected body zones;

a female connector defining an opening in the peripheral surface leading to a channel within the single monolithic piece, wherein the female connector provides for receiving the male connector therein providing for the electrical power module to provide electrical current to the opposite body zone engaging faces.

* * * * *